United States Patent [19]

Yamamori et al.

[11] Patent Number: 5,298,569

[45] Date of Patent: * Mar. 29, 1994

[54] METALLIC ESTER ACRYLIC COMPOSITIONS CAPABLE OF RELEASING BIOACTIVE SUBSTANCE AT A CONTROLLED RATE

[75] Inventors: Naoki Yamamori; Hiroharu Ohsugi; Yoshio Eguchi, all of Osaka; Junji Yokoi, Nara, all of Japan

[73] Assignee: Nippon Paint Co., Osaka, Japan

[ * ] Notice: The portion of the term of this patent subsequent to Sep. 27, 2005 has been disclaimed.

[21] Appl. No.: 1,417

[22] Filed: Jan. 7, 1993

Related U.S. Application Data

[63] Continuation of Ser. No. 622,112, Dec. 5, 1990, abandoned, which is a continuation of Ser. No. 267,698, Nov. 3, 1988, abandoned, which is a continuation of Ser. No. 924,823, Oct. 30, 1986, abandoned.

[30] Foreign Application Priority Data

Oct. 30, 1985 [JP] Japan .................. 60-243593

[51] Int. Cl.$^5$ .................... C08F 8/42; C08F 220/04
[52] U.S. Cl. ................ 525/329.5; 424/78.08; 424/78.34; 525/330.2; 525/366; 525/370; 526/240; 526/241

[58] Field of Search ............. 525/329.5, 327.8, 328.5, 525/330.2, 366, 370, 372; 526/240, 241, 204, 205, 215, 239

[56] References Cited

U.S. PATENT DOCUMENTS

| | | | |
|---|---|---|---|
| 3,886,125 | 5/1975 | Chromocek | 526/240 |
| 4,429,094 | 1/1984 | Massuco | 526/240 |
| 4,562,234 | 12/1985 | Besecke | 526/241 |
| 4,774,080 | 9/1988 | Yamamori | 424/78.09 |

FOREIGN PATENT DOCUMENTS

| | | |
|---|---|---|
| 696 | 3/1962 | Japan . |
| 23867 | 10/1968 | Japan . |
| 41468 | 12/1971 | Japan . |
| 164608 | 9/1983 | Japan . |

Primary Examiner—Christopher Henderson
Attorney, Agent, or Firm—Wenderoth, Lind & Ponack

[57] ABSTRACT

A bioactive substance control-releasing resinous composition comprising a resin having main chain and side chains, at least one side chain bearing at the end portion thereof an organic acid moiety having a biological activity, through a metal ester bonding. The resin is hydrolyzed in an ionic atmosphere at a controlled rate to generate a bioactive substance as well as metal ions and is useful in various fields and especially as a resinous vehicle for a coating composition.

2 Claims, No Drawings

METALLIC ESTER ACRYLIC COMPOSITIONS CAPABLE OF RELEASING BIOACTIVE SUBSTANCE AT A CONTROLLED RATE

This application is a continuation of now abandoned application Ser. No. 07/622,112, filed on Dec. 5, 1990, which is a continuation of now abandoned application Ser. No. 07/267,698, filed on Nov. 3, 1988, which is a continuation of now abandoned application Ser. No. 06/924,823, filed on Oct. 30, 1986.

FIELD OF INVENTION

The present invention relates to a resinous composition capable of releasing a bioactive substance at a controlled rate, and more specifically, it concerns a resinous composition comprising a resin, to which an organic acid having a biological activity is incorporated through a metal ester bond at the end portion of at least one side chain thereof, and capable of releasing, under mild conditions, a bioactive substance at a controlled rate for a longer duration of time.

BACKGROUND OF THE INVENTION

Today, various bioactive substances are used in agricultural, medical or other fields, and however, since they are usually employed in larger quantities because of their poor migration to the target, short retention time and easy scattering in air coming from their characteristic properties such as hydrophilic properties hydrophobic properties volatility and the like, fears are always entertained for the safety of such materials, e.g. soil contamination in case of agricultural chemicals, undesired side-effects in case of medicines and the like.

Attempts, therefore, have been made to make a high polymer carrying a bioactive substance, from which the said bioactive substance is released at a controlled rate, thereby attaining the desired effect for a long period of time and obviating the useless, excessive release of the active substance (see, for example, Japanese Patent Application Kokai No. 143326/82).

However, in these attempts, the carrying of bioactive substance on the high polymer was relied on a covalent bond, and therefore, for the release of such substance, hydrolysis under a high temperature and a highly acidic or basic atmosphere had always been required, as well as a long reaction time. Since the hydrolysis rate is very low under mild conditions as in human body, soil, sea water and the like and the desired slow releasing at a controlled rate is hardly obtainable with these products, they have never been put to practical use up to the present time.

An object of the present invention is, therefore, to provide a resin carrying a bioactive substance, from which the said substance is gradually released at a controlled rate through hydrolysis under mild conditions. An additional object of the invention is to provide a resinous composition containing said resin.

SUMMARY OF THE INVENTION

According to the present invention, the aforesaid objects can be attained with a resinous composition comprising a resin having both main chain and side chains, at least one side chain bearing at the end portion thereof an organic acid moiety having a biological activity through a metal ester bonding.

More specifically, the said side chain may carry, at the end portion, with at least one group represented by the formula:

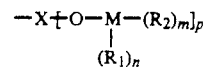

wherein X is

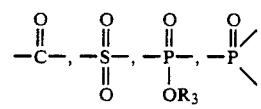

or an aromatic residue; M is a metal whose valency is 2 or more; p is an integer of 1 to 2; m is an integer of 1 or more; n is 0 or an integer of 1 or more, providing satisfying the condition that $m+n+1$ is equal to the metal valency; $R_1$ is a hydrocarbon residue having 1 to 10 carbon atoms; $R_2$ is a reside of organic acid having a biological activity which is connected through $$-S-\overset{S}{\underset{\parallel}{C}}-,\ -O-\overset{O}{\underset{\parallel}{C}}-,\ -O-\overset{S}{\underset{\parallel}{C}}-,\ -S-,\ -O-\ \text{or}\ -O-\overset{O}{\underset{\underset{O}{\parallel}}{S}}-$$

bond to the metal M; and $R_3$ is hydrogen or a hydrocarbon residue having 1 to 10 carbon atoms.

Preferred Embodiments of the Invention

The present resinous composition is characterized by comprising a novel resin having at the end portion of at least one side chain at least one group represented by the aforesaid formula and capable of releasing, through hydrolysis under mild conditions, at a controlled rate, a bioactive substance therefrom.

Such resinous composition may be advantageously prepared by either one of the following methods.

That is, one method comprises preparing a polymerizable unsaturated monomer having at the end portion a metal ester of an organic acid having a biological activity, and copolymerizing the same with other polymerizable monomers, and the other method comprises reacting an acid group bearing polymer, obtained by the reaction of an acid group bearing monomer and other polymerizable monomer, with a metal-oxide, -chloride or -hydroxide and a monovalent organic acid having a biological activity, or subjecting said acid group bearing polymer to an ester exchange reaction with a metal ester of said monovalent organic acid. More specifically, the present resinous composition may be prepared by either of the following methods.

(1) A mixture of
 (a) a metal oxide, a metal hydroxide, a metal sulfide or a metal chloride,
 (b) a monovalent organic acid having a biological activity or an alkali metal salt thereof, and
 (c) a polymerizable organic acid or an alkali metal salt thereof, is heated, under stirring, at a temperature of less than the decomposition temperature of said metal salt, and the by-produced alkali metal chloride, water, metal ester of said monovalent organic acid, and metal ester of bifunctional, polymerizable organic acid are separated as desired, to obtain a metal ester of said polymerizable organic acid and said monovalent organic acid having a biological activity. In the abovesaid reaction, it is not always necessary to use equimolar amounts of (a), (b) and (c), and one may use 0.3 to 3 equivalent (b) and 0.8 to 2 equivalent (c) per 1 equivalent (a) to obtain the desired ester.

(2) Alternatively, a mixture of
(d) a resin having at a side chain an organic acid or its alkali metal salt,
(e) a metal oxide, a metal hydroxide, a metal sulfide or a metal chloride, and
(f) a bioactive, monovalent organic acid is heated, under stirring, at a temperature of lower than the decomposition temperature of said (e) and the by-produced products are separated to obtain a resin having at a side chain the desired metal ester moiety.

In this reaction, it is preferred to use 0.8 to 1.5, most preferably 1.0 to 1.2, equivalent (e) and 0.8 to 2, most preferably 1.0 to 1.5, equivalent (f) per 1 equivalent organic acid in said (d) resin.

When a low boiling monovalent organic acid is selected and the involved reaction is accompanied with a dehydration, there is a risk that an amount of said monovalent organic acid is distilled out of the system with the formed water and the undesired metal ester bondings are formed between the resin molecules. Therefore, under such circumstances it is preferred to use a larger quantities of said monovalent organic acid and to prevent undue increase in viscosity or gelation of the reaction mixture.

(3) In an another method, a resin having at a side chain an organic acid (g) is reacted with a metal ester of bioactive, monovalent organic acid (h) at a temperature lower than the decomposition temperature thereof, to introduce the metal ester moiety at the end portion of said side chain through an ester exchange reaction. At this time, when a low boiling monovalent organic acid (as acetic acid) is selected, the reaction must be proceeded very carefully because of the possibility of the acid being lost out of the system and the formation of metal ester bond between the resinous molecules. Usually, 0.3 to 3 equivalent, preferably 0.4 to 2.5 equivalent, (h) is used for 1 equivalent organic acid in resin (g).

As to the polymerizable organic acid (c) to be used in the abovementioned method, mention is made of methacrylic acid, acrylic acid, p-styrene sulfonic acid, 2-methyl-2-acrylamide propane sulfonic acid, methacrylic acid phosphoxy propyl, methacrylic acid 3-chloro-2-acidphosphoxy propyl, methacryl acid phosphoxy ethyl, itaconic acid, maleic acid and anhydride thereof, monoalkyl itaconate (e.g. methyl, ethyl, butyl, 2-ethyl hexyl and the like), monoalkyl maleate (e.g. methyl, ethyl, butyl, 2-ethyl hexyl and the like); half ester of acid anhydride with HO bearing polymerizable monomer, as, for example, half esters of succinic anhydride, maleic anhydride, phthalic anhydride or the like with 2-hydroxyethyl (meth) acrylate. Each is used alone or in a combination of 2 and more.

As the bioactive substance (b), any of the aliphatic, aromatic, alicyclic or heterocyclic acids known to be useful as medicines, agricultural chemicals, repellents, bactericides, anti-bacterial agent, fungicides, antibiotics, perfumes, antiseptics and the like, are satisfactorily used. Examples of such materials (b) are as follows:

(1)

containing acid: alicyclic carboxylic acids as chaulmoogric acid, hydnocarpusic acid and the like; aromatic carboxylic acids as salicylic acid, cresotic acid, naphthoic acid, p-oxybenzoic acid, benzoic acid, mandelic acid, dibromosalicylic acid, cinnamic acid, capro chlorone, nitrobenzoic acid, 2,4-dichloro-phenoxy acetic acid, 2,4,5-trichloro-phenoxy acetic acid, nitronaphthalene carboxylic acid, aspirin, nicotinic acid and the like; lactone series carboxylic acids as pulvinic acid, and the like; uracil derivatives as uracil-4-carboxylic acid, 5-fluorouracil-4-carboxylic acid, uracil-5-carboxylic acid and the like; carboxylic acids with penicillin structure as penicillin U, Ampicillin, penicillin BT, penicillanic acid, penicillin G, penicillin O and the like; sarcomycin, chloramphenicol, variotin, Rifamycin B, Lusonsomycin and the like.

An alcoholic hydroxyl containing, bioactive substance may be treated with an acid anhydride (e.g. succinic anhydride, maleic anhydride, phthalic anhydride, tetrahydro phthalic anhydride) to give a half-ester product, which may be used as

containing acid. Examples of such alcoholic hydroxyl containing, bioactive substances are testosterone, uridine, thymidine, L-menthol, cinnamic alcohol, benzyl alcohol, maltol, linalool, dimethyl benzyl carbinol, rhodinol and the like.

(2)

containing acid: dithiocarbamates as dimethyl dithiocarbamate and the like.

(3)

containing acid: Sulfur containing aromatic compounds as 1-naphthol-4-sulfonic acid, p-phenyl benzene sulfonic acid, β-naphthalene sulfonic acid, quinoline sulfonic acid and the like.

(4)

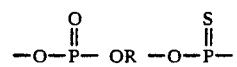

containing acid: Triethyl-pyrophosphate, dimethylaminophosphate, and other organo-phosphoric compounds.

(5) —S— containing acid: Compounds having

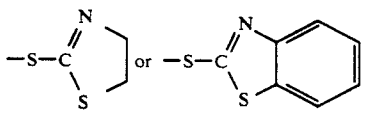

group.

(6)

containing acid: Thiocarboxylic acids.

(7) —O— containing acid: Phenols as phenol, cresol, xylenol, thymol, carvacrol, eugenol, phenyl phenol, benzyl phenol, guaiacol, pterstilbene, (di) nitrophenol, nitrocresol, methyl salicylate, benzyl salicylate, (mono-, di-, tri-, tetra- or penta-) chlorophenol, chlorocresol, chloroxylenol, chlorothymol, p-chloro-O-cyclohexyl phenol, p-chloro-O-cyclopentyl phenol, p-chloro-O-n-hexyl phenol, p-chloro-O-benzyl phenol, p-chloro-O-benzyl-m-cresol and the like; and β-naphthol, 8-hydroxy quinoline and the like.

These are typical examples of the employable organic acid and the invention can never be limited to the exemplified members only. In the present invention, any of the organic acids may be satisfactorily used, providing exhibiting a biological activity, for example, in a conventional anti-bacterial activity test (e.g. paper-disc method). As the metal source, any of the metals having a valency of 2 or more may be satisfactorily used, including Ca, Mg, Zn, Cu, Ba, Te, Pb, Fe, Co, Ni, Bi, Si, Ti, Mn, Al and Sn. However, in the present invention, metal ions are likewise produced by the hydrolysis of the present resin and such ions may give additional function, depending on the metal species. Therefore, it is preferred to select an appropriate metal source depending on the properties of metal ions and the intended objects of the resulted resin. As the metal source which will give the resin with a comparatively slow hydrolysis rate, mention is made of Ca, Mg and Al.

Examples of such metals as giving bioactive metal ions are Cu, Zn, Te, Ba, Pb and Mn and examples of metals which will give the ions with no bioactivity are Si and Ti. Such metals as Cu, Fe, Co, Ni and Mn are known as coloring metals.

Usually, they are used in the form of oxides, hydroxides or chlorides, and however, other halogenides, sulfides and carbonates may also be employed as desired.

As the polymerizable monomer to be reacted with said metal ester of the polymerizable organic acid and the monovalent bioactive organic acid, any of the known copolymerizable monomers may be satisfactorily used. Examples of such monomers are methyl (meth) acrylate, ethyl (meth) acrylate, propyl (meth) acrylate, butyl (meth) acrylate, octyl (meth) acrylate, 2-ethyl hexyl (meth) acrylate, styrene, vinyl toluene, vinyl pyridine, vinyl pyrrolidone, vinyl acetate, acrylonitrile, methacrylonitrile, dimethyl itaconate, dibutyl itaconate, di-2-ethyl hexyl itaconate, dimethyl maleate, di-(2-ethyl hexyl) maleate, ethylene, propylene, vinyl chloride and the like. If desired, one may use hydroxyl bearing monomers as, for example, 2-hydroxy ethyl (meth) acrylate, 2-hydroxy propyl (meth) acrylate and the like.

Examples of the resin (d) or (g) having at a side chain an organic acid, are acid bearing-vinyl resins -polyester resins, -oil modified alkyd resins, -fatty acid modified alkyd resins, -epoxy resins and the like. In the present resin having at the end portion of at least one side chain a monovalent, bioactive organic acid metal ester, every organic acids at the side chains need not participate in such metal ester bonding and some of the acids may be left intact, in free acid form, as desired. The invention shall be now more fully explained in the following Examples. Unless otherwise being stated, all parts and percentages are by weight.

SYNTHESIS OF RESIN SOLUTION

SYNTHETIC EXAMPLE 1

Into a four necked flask fitted with a stirrer, a reflux condenser and a dropping funnel, were placed 120 parts of xylene and 30 parts of n-butanol and the mixture was maintained at 110° to 120° C.

To this, was dropwise added at a constant speed a mixture of 60 parts of ethyl acrylate, 25 parts of 2-ethyl hexyl acrylate, 15 parts of acrylic acid, and 2 parts of azobisisobutyronitrile in 3 hours and the mixture was maintained at 110° to 120° C. for 2 hours, to obtain a resin solution A having a solid content of 39.8% and a viscosity of 2.2 poises.

SYNTHETIC EXAMPLE 2

Into a similar reaction vessel as used in Synthetic Example 1, were placed 75 parts of xylne and 75 parts of n-butanol and the mixture was maintained at 110° C. To this, was dropwise added a mixture of 50 parts of n-butyl methacrylate, 45 parts of methyl methacrylate, 5 parts of methacrylic acid and 2 parts of benzoyl peroxide in 3 hours and thereafter, the combined mixture was maintained at 110° C. for 2 hours. Thus obtained mixture has a solid content of 39.8% and a viscosity of 0.8 poise. To this, 46 parts of 5 wt % solution of sodium hydroxide in methanol were added to obtain a resin solution B.

SYNTHETIC EXAMPLE 3

Into a four necked flask fitted with a stirrer, a reflux condenser and a dropping funnel, were placed 70 parts of xylene and 30 parts of methyl isobutyl ketone and the mixture was maintained at 115° to 120° C. To this, was dropwise added at a constant speed a mixture of 40 parts of 2-ethyl hexyl methacrylate, 55 parts of methyl methacrylate, 5 parts of methacrylic acid and 2.2 parts of azobisisobutyronitrile in 3 hours and the combined mixture was maintained at the same temperature for 2 hours. Thus obtained resin solution C had a solid content of 49.8% and a viscosity of 3.6 poises.

EXAMPLE 1

Into a similar reaction vessel as used in Synthetic Example 2, were placed 100 parts of toluene, 172 parts of barium hydroxide, 86 parts of methacrylic acid, and 167 parts of nitro benzoic acid and the mixture was reacted, under air bubbling condition and while removing the formed water, at 120° C. for 3 hours. After removing undissolved materials, a green colored toluene solution was obtained. Vinyl group and barium carboxylate were confirmed by the IR inspection of the solid matter.

Into a similar reaction vessel as used in Synthetic Example 1, were placed 100 parts of said toluene solution and 150 parts of xylene and the mixture was heated to 100° C. To this, was dropwise added a mixture of 150 parts of methyl methacrylate and 2 parts of azobisisobutyronitrile in 3 hours and the combined mixture was maintained at the same temperature for 2 hours. Thus obtained resin solution had a solid content of 55.9 wt % and a viscosity (at 25° C.) of 2.3 poises.

The resin solution was then treated with methanol to precipitate the contained resin and thus a purified resin R-1 was obtained. Barium content of the resin was analyzed by a fluorescent X ray method and was found to be 5.2 wt %. By a UV spectrophotometry, the presence of nitrobenzoic acid in the resin was confirmed.

EXAMPLE 2

Into a four necked flask fitted with a stirrer, a reflux condenser and a decanter, were placed 100 parts of the resin solution A, 11.5 parts of salicylic acid, and 7.5 parts of ferric hydroxide and the mixture was heated to 120° C. and thereafter, maintained at the same temperature, while removing the formed water (total dehydration 2.8 parts H₂O), for 2 hours. After filtration, the contained resin was precipitated by white spirit to obtain the purified resin. Using the similar analytical method, Fe content was determined to be 3.9 wt %. The presence of salicylic acid was confirmed by a UV absorption and the presence of two aromatic substituents by IR spectrum of the resin. This resin was referred to R-2 hereinunder.

EXAMPLE 3

Into a similar reaction vessel as used in Example 2, were placed 150 parts of the resin solution A, 17.3 parts of salicylic acid and 30.2 parts of lead hydroxide and the mixture was heated to 120° C. and maintained at the same temperature for 2 hours, while removing the formed water (total dehydration 4.2 parts H₂O).

The resin solution was then reprecipitated and purified as in Example 2 and the lead content of the resin was analyzed as in Example 1. It was confirmed that the lead content was 6.8 wt %. The presence of salicylic acid in said resin was confirmed by UV absorption of the acid and the presence of two aromatic substituents by IR inspection means. Thus obtained resin was referred to as R-3.

EXAMPLE 4

Into a similar reaction vessel as used in Example 2, were placed 100 parts of the resin solution A, 14.4 parts of 5-quinoline carboxylic acid and 7.7 parts of nickel hydroxide and the mixture was heated to 120° C. and maintained at the same temperature for 2 hours, while removing the formed water (total dehydration 2.7 parts H₂O). The resin solution was then filtered and treated in the same way as stated in Example 2. The nickel content was analyzed as in Example 1 and determined to be 3.5 wt %. The resin was referred to as R-4.

EXAMPLE 5

Into a four-necked flask fitted with a stirrer and a reflux condenser, were placed 100 parts of the resin solution B, 3.7 parts of sodium salicylate and 6.2 parts of mercurous chloride and the mixture was reacted at 120° C. for 2 hours. Thus obtained resin solution was filtered and treated in the same way as stated in Example 2. The mercury content of the resin was 3.6 wt %. The resin was referred to as R-5.

EXAMPLE 6

Into a similar reaction vessel as used in Example 5, were placed 150 parts of the resin solution B, 4.0 parts of sodium monochloracetate and 4.5 parts of nickel chloride and the mixture was reacted at 120° C. for 2 hours. Thus obtained resin solution was filtered and treated in the same way as stated in Example 2, to obtain the resin R-6 having the nickel content of 1.0 wt %.

EXAMPLE 7

Into a similar reaction vessel as stated in Example 5, were placed 100 parts of the resin solution B, 6.5 parts of sodium triethylpyrophosphate and 3.0 parts of nickel chloride and the mixture was filtered and treated in the same way as stated in Example 2. The nickel content of the resin was 0.9 wt %. This resin was referred to as R-7.

EXAMPLE 8

Into a similar reaction vessel as used in Example 2, were placed 100 parts of the resin solution A, 18.1 parts of nitro naphthalene carboxylic acid and 6.5 parts of aluminium hydroxide and the mixture was heated to 120° C. and maintained at the same temperature for 2 hours, while removing the formed water (dehydration 2.6 parts H₂O). The resin solution was filtered and treated in the same way as stated in Example 2. The aluminium content of the resin was 1.8 wt %. This resin was referred to as R-8.

EXAMPLE 9

Into a similar reaction vessel as used in Synthetic Example 1, were placed 100 parts of toluene, 89 parts of manganese hydroxide, 86 parts of methacrylic acid, and 221 parts of 2,4-dichlorophenoxy acetic acid and the mixture was reacted, while bubbling air and removing the formed water, at 120° C. for 3 hours.

Next, the undissolved materials were filtered off to obtain a green colored toluene solution.

From the IR spectrum analysis, vinyl group and Mn carboxylate in the solid matter of said toluene solution were confirmed.

Into a similar reaction vessel as used in Synthetic Example 1, were placed 100 parts of said toluene solution and 200 parts of xylene and the mixture was heated to 100° C. To this, 150 parts of methyl methacrylate and 2 parts of azobisisobutyronitrile were dropwise added in 3 hours and the combined mixture was maintained at the same temperature for 2 hours. Thus obtained resin solution was filtered and treated in the same way as stated in Example 2. The manganese content of the resin was 1.5 wt %. This resin was referred to as R-9.

EXAMPLE 10

Into a similar reaction vessel as used in Example 1, were placed 100 parts of the resin solution A, 16.1 parts of benzene sulfonic acid chloride and 14.3 parts of barium hydroxide, and the mixture was heated to 120° C. and maintained at the same temperature, while removing the formed water, for 2 hours (dehydration 2.5 parts H₂O). The resin solution was then filtered and treated in the same way as stated in Example 2. The barium content of the resin was analyzed as in Example 1 and determined to be 7.9 wt %. This resin was referred to as R-10.

EXAMPLE 11

Into a similar reaction vessel as used in Synthetic Example 1, were placed 100 parts of toluene, 90 parts of iron hydroxide, 86 parts of methacrylic acid and 152 parts of dimethylaminophosphate and the mixture was reacted at 120° C. for 3 hours, while bubbling air and removing the formed water therefrom.

The undissolved materials were then filtered off to obtain a green colored toluene solution. By the IR spectrum analysis, vinyl group and iron carboxylate in the solid matter of said toluene solution were confirmed. Into a similar reaction vessel as used in Synthetic Example 1, were placed 100 parts of said toluene solution and 150 parts of xylene and the mixture was heated to 100° C. To this, were dropwise added 150 parts of methyl methacrylate and 2 parts of azobisisobutyronitrile in 3 hours and the combined mixture was maintained at 100° C. for 2 hours. Thus obtained resin solution was filtered and treated in the same way as stated in Example 2. The iron content of the resin was analyzed as in Example 1 and confirmed to be 2.9 wt %. The resin was referred to as R-11.

EXAMPLE 12

Into a four-necked flask fitted with a stirrer and a reflux condenser, were placed 100 parts of the resin solution B, 4.0 parts of sodium diethyl dithio carbamate and 3.0 parts of nickel chloride and the mixture was reacted at 120° C. for 2 hours.

Thus obtained resin solution was filtered and treated as in Example 2. The nickel content of the resin was analyzed as in Example 2 and confirmed to be 0.9 wt %. This resin was referred to as R-12.

EXAMPLES 13 to 25

Using the procedures of Example 2 or 5 and following the prescriptions shown in Table 1, various resins (R-13 to R-25) were prepared. The metal contents of these resins are shown in Table 1.

EXAMPLE 26

Into a reaction vessel fitted with a stirrer and a vacuum distillation means, were placed 25 parts of the resin solution C, 2.5 parts of Penicillin V and 5 parts of barium hydroxide and the mixture was heated to 90° C. and maintained at the same temperature, while removing the formed water, for 40 minutes. Thus obtained resin solution was filtered and treated in the same way as stated in Example 2. The barium content of the resin was 18.2 wt %. This resin was referred to as R-26.

EXAMPLE 27 to 30

Using the same procedures as stated in Example 26 and following the prescription shown in Table 1, the resins R-27 to R-30 were prepared. The metal Contents of these resins are shown in Table 1.

TABLE 1

| | Example | | | | | | | | | | |
|---|---|---|---|---|---|---|---|---|---|---|---|
| | 13 | 14 | 15 | 16 | 17 | 18 | 19 | 20 | 21 | 22 | 23 |
| resin solution A | 100 | 100 | 100 | 100 | 100 | 100 | 100 | 100 | 100 | 100 | 100 |
| barium hydroxide | 14.2 | | | | | 14.2 | | 14.2 | | | |
| magnesium hydroxide | | 4.8 | | | | | | | | | |
| calcium hydroxide | | | 6.0 | | | | | | | | |
| copper hydroxide | | | | 8.1 | 8.1 | | 8.1 | | 8.1 | | |
| bismuth hydroxide | | | | | | | | | | 14.0 | |
| titanium oxide | | | | | | | | | | | 6.2 |
| L-menthol/succinic anhydride half-ester | 21.2 | | | | | | | | | | |
| uridine/succinic anhydride half-ester | | 28.6 | | | | | | | | | |
| citronellol/succinic anhydride half-ester | | | 21.2 | | | | | | | | |
| geranol/succinic anhydride half-ester | | | | 20.9 | | | | | | | |
| testosteron/maleic anhydride half-ester | | | | | 32.4 | | | | | | |
| eugenol | | | | | | 13.6 | | | | | |
| 8-hydroxyquinoline | | | | | | | 12.0 | 12.0 | | | 36.0 |
| β-naphthol | | | | | | | | | 12.0 | | |
| thymol | | | | | | | | | | 22.0 | |
| resin | R-13 | R-14 | R-15 | R-16 | R-17 | R-18 | R-19 | R-20 | R-21 | R-22 | R-23 |
| metal content (wt %) | 15.1 | 2.6 | 5.1 | 7.8 | 6.2 | 16.8 | 8.9 | 15.7 | 8.6 | 20.1 | 6.6 |
| Example (preparation) | 2 | 2 | 2 | 2 | 2 | 2 | 2 | 2 | 2 | 2 | 2 |

| | Example | | | | | |
|---|---|---|---|---|---|---|
| | 24 | 25 | 27 | 28 | 29 | 30 |
| resin solution A | 100 | | | | | 100 |
| resin solution B | | 50 | | | | |
| resin solution C | | | 25 | 25 | 25 | |
| barium hydroxide | | | 5.0 | 5.0 | 5.0 | |
| zinc chloride | | 3.4 | | | | |
| tellurium dioxide | 13.0 | | | | | |
| dibutyl tin oxide | | | | | | 21.0 |
| 8-hydroxyquinoline | 38.0 | | | | | |
| Penicillin V | | | | | | |
| Penicillin G Ka | | 9.3 | | | | |
| 5-fulorinated uracil-4-carboxylic acid | | | 1.3 | | | |
| uracil-4-carboxylic acid | | | | 1.2 | | |
| sarcomycin | | | | | 1.1 | |
| 5-quinoline carboxylic acid | | | | | | 14.4 |
| resin | R-24 | R-25 | R-27 | R-28 | R-29 | R-30 |
| metal content (wt %) | 10.1 | 1.1 | 20.3 | 20.4 | 21.0 | 5.1 |
| Example (preparation) | 2 | 5 | 26 | 26 | 26 | 2 |

COMPARATIVE EXAMPLE 1

Into a similar reaction vessel as used in Example 2, were placed 100 parts of the resin solution A, 6.2 parts of titanium dioxide and 70 parts of stearic acid and the mixture was heated to 120° C. and reacted at the same temperature, while removing the formed water, for 2 hours. The resin solution was hot-filtered, extracted with hot n-hexane, and purified by re-precipitation means to obtain a comparative resin A. The titanium content of the resin was 4.8 wt %.

COMPARATIVE EXAMPLE 2

Into a similar reaction vessel as used in Synthetic Example 1, were placed 120 parts of xylene and 30 parts of n-butanol and the mixture was maintained at 110° to 120° C. To this, was dropwise added a mixture of 40 parts of methyl methacrylate, 30 parts of 2-ethyl hexyl methacrylate, 30 parts of glycidyl methacrylate and 2.3 parts of benzoyl peroxide in 3 hours and the combined mixture was maintained at the same temperature for 2 hours. Next, 32 parts of 5-quinoline carboxylic acid and 0.8 part of triethylamine were added and the combined mixture was reacted at 120° to 125° C. The esterification reaction ws traced by the amounts of unreacted 5-quinoline carboxylic acid remained in the reaction system by an alkali titration and the reaction was stopped at the stage when the reaction rate of 98% or more was obtained.

The resin solution was added with ethanol to precipitate the contained resin and thus purified resin was referred to as Comparative resin B.

PREPARATION OF RESIN SOLUTION

Each resin obtained in Examples 1 to 30 and Comparative Examples 1 to 2 was dissolved in tetrahydrofuran to give 20 wt % resin solution, which was used as sample solution in the following tests.

BIOACTIVE SUBSTANCE CONTROL RELEASE TEST

The sample solution was applied on a glass plate (40 mm × 70 mm) and dried so as to give about 500 mg total resin. Thus prepared glass plate was dipped in 500 ml of sodium phosphate buffer (pH=7.2) and the control release rate of the contained active substance at 40° C. was examined. That is, a small amount of said buffer solution was taken from time to time and subjected to a liquid chromatography. The active substance control release rate was determined by comparing the intensity ratio of the active substance in the pick-up buffer solution and the intensity ratio of the internal standard compound (glycerin) previously added to said buffer in a concentration of 150 mg/500 ml and using the following equation.

Active substance control release rate =

$$\frac{\text{active substance intensity ratio}}{\text{glycerin intensity ratio}} \times 100 \div \text{dipping days}$$

The results are shown in Table 1.

At the same time, the released amounts of metal ions per day was determined by taking a measurement of metal content in 100 ml buffer solution, using an atomic-absorption spectroscopy.

BIOACTIVITY CONTROL RELEASE TEST

Bioactive substance detecting disc culture medium (Kyokutosha, 2% aqueous solution) was sterilized at 120° C. for 30 minutes and mixed with broth on which Bacillus sp., Vibrio sp. or Salmenella sp. had been previously inoculated and cultured, in a weight ratio of 5:1, and an agar plane culture was thus prepared.

A paper disc having a diameter of about 7 mm (prepared by Toyo filter paper No. 53) was dipped in a sample solution and dried. This paper disc was then placed on said plane culture and the medium was cultured at 30° C. for 1 week. From the diameter of bacterial growth inhibition circle, an antibacterial activity of the tested material was determined.

Next, the said paper disc was washed with a purified and heat-sterilized water and dried. By using the washed paper disc, the abovesaid antibacterial activity test was repeated with a fresh culture medium.

The same procedures were repeated. The test results with Bacillus sp. are shown in Table 2.

In another series of tests with Vibrio sp. and Salmonella sp., the similar test results with those with Bacillus sp. were obtained, i.e. clear inhibition circles with the resins of Examples 1 to 30 but no inhibition circles with the resins of Comparative Examples 1 to 2 after 2 weeks repeating tests.

TABLE 2

Active substance control release test

| | Example | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| active substance released | | | | | | | | | | | | | | | | | | | | | | | | |
| after 3 days | 5.4 | 6.2 | 5.8 | 6.4 | 2.1 | 2.4 | 2.5 | 3.2 | 3.8 | 5.4 | 6.3 | 2.7 | 9.8 | 5.2 | 6.0 | 6.6 | 6.2 | 9.7 | 6.4 | 8.3 | 6.2 | 10.4 | 9.8 | 11.6 |
| after 5 days | 4.8 | 5.3 | 5.1 | 6.1 | 1.9 | 1.7 | 2.2 | 3.0 | 3.2 | 5.1 | 5.8 | 2.2 | 9.2 | 4.8 | 5.8 | 5.8 | 5.6 | 9.4 | 6.0 | 8.0 | 5.8 | 9.6 | 9.1 | 10.2 |
| after 10 days | 4.9 | 5.1 | 4.9 | 5.8 | 1.9 | 1.5 | 2.0 | 3.0 | 3.4 | 4.9 | 5.9 | 2.0 | 9.0 | 4.7 | 5.8 | 5.9 | 5.6 | 9.1 | 6.0 | 7.9 | 5.9 | 9.2 | 9.2 | 10.4 |
| after 20 days | 4.7 | 5.4 | 5.0 | 6.0 | 1.6 | 1.5 | 2.0 | 3.1 | 3.6 | 5.0 | 5.9 | 2.1 | 9.0 | 4.8 | 5.6 | 5.9 | 5.7 | 8.9 | 5.9 | 8.0 | 5.7 | 9.3 | 8.8 | 10.6 |
| after 40 days | 4.7 | 5.0 | 5.2 | 5.7 | 1.7 | 1.4 | 2.0 | 3.0 | 3.5 | 4.9 | 6.0 | 2.0 | 8.9 | 4.6 | 5.7 | 5.7 | 5.5 | 8.9 | 5.8 | 7.8 | 5.7 | 8.8 | 8.6 | 9.8 |
| metal amounts released | | | | | | | | | | | | | | | | | | | | | | | | |
| after 3 days | 1.5 | 1.8 | 1.2 | 0.9 | 1.0 | 0.3 | 0.3 | 0.4 | 0.6 | 1.8 | 1.2 | 0.4 | 3.6 | 1.2 | 1.6 | 1.8 | 1.6 | 4.2 | 1.8 | 4.4 | 1.7 | 5.2 | 1.5 | 2.1 |
| after 5 days | 1.3 | 1.4 | 0.9 | 0.6 | 0.8 | 0.3 | 0.2 | 0.3 | 0.5 | 1.6 | 1.0 | 0.3 | 3.2 | 1.0 | 1.5 | 1.3 | 1.3 | 3.9 | 1.4 | 4.0 | 1.4 | 4.6 | 1.2 | 1.7 |
| after 10 days | 1.3 | 1.4 | 0.7 | 0.7 | 0.6 | 0.2 | 0.3 | 0.3 | 0.3 | 1.6 | 1.0 | 0.2 | 3.0 | 0.8 | 1.4 | 1.4 | 1.3 | 3.7 | 1.5 | 3.8 | 1.4 | 4.4 | 1.2 | 1.8 |
| after 20 days | 1.2 | 1.2 | 0.8 | 0.6 | 0.7 | 0.2 | 0.2 | 0.3 | 0.4 | 1.5 | 1.0 | 0.2 | 3.1 | 0.8 | 1.4 | 1.3 | 1.4 | 3.8 | 1.4 | 3.8 | 1.5 | 4.5 | 1.3 | 1.7 |
| after 40 days | 1.2 | 1.3 | 0.8 | 0.6 | 0.7 | 0.2 | 0.2 | 0.3 | 0.4 | 1.5 | 1.0 | 0.2 | 3.1 | 0.8 | 1.4 | 1.3 | 1.2 | 3.8 | 1.3 | 3.8 | 1.3 | 4.2 | 1.2 | 1.9 |

| | Example and Comparative Example | | | | | | | |
|---|---|---|---|---|---|---|---|---|
| | | | | | | | Comp. Ex. | |
| | 25 | 26 | 27 | 28 | 29 | 30 | 1 | 2 |
| active substance liberated | | | | | | | | |
| after 3 days | 2.2 | 2.8 | 2.6 | 2.7 | 2.6 | 9.8 | 8.8 | <0.1 |
| after 5 days | 1.9 | 2.3 | 2.4 | 2.3 | 2.3 | 9.2 | 8.2 | <0.1 |
| after 10 days | 1.7 | 2.3 | 2.4 | 2.3 | 2.4 | 8.8 | 8.2 | <0.1 |
| after 20 days | 1.7 | 2.4 | 2.5 | 2.1 | 2.1 | 8.8 | 8.0 | <0.1 |
| after 40 days | 1.8 | 2.4 | 2.2 | 2.2 | 2.0 | 9.0 | 8.0 | <0.1 |

TABLE 2-continued

Active substance control release test

| | metal amounts liberated | | | | | | | | |
|---|---|---|---|---|---|---|---|---|---|
| | after 3 days | 0.8 | 1.9 | 2.2 | 1.8 | 2.0 | 1.9 | 1.3 | 0 |
| | after 5 days | 0.6 | 1.7 | 1.9 | 1.6 | 1.8 | 1.7 | 1.1 | 0 |
| | after 10 days | 0.6 | 1.7 | 1.8 | 1.6 | 1.8 | 1.7 | 1.1 | 0 |
| | after 20 days | 0.4 | 1.8 | 1.8 | 1.7 | 1.6 | 1.7 | 1.2 | 0 |
| | after 40 days | 0.4 | 1.6 | 1.7 | 1.7 | 1.7 | 1.7 | 1.1 | 0 |

TABLE 3

Bioactivity control release test

| | Example | | | | | | | | | | | | | | | | | | | | | |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| After 1 week (mm) | 13 | 12 | 16 | 13 | 20 | 10 | 11 | 12 | 14 | 13 | 16 | 10 | 14 | 16 | 11 | 15 | 11 | 10 | 17 | 11 | 16 | 13 |
| 2 weeks (mm) | 11 | 10 | 14 | 12 | 18 | 9 | 9 | 10 | 12 | 12 | 13 | 8 | 12 | 15 | 10 | 13 | 9 | 8 | 15 | 9 | 15 | 11 |
| 3 weeks (mm) | 11 | 10 | 14 | 12 | 18 | 9 | 9 | 10 | 12 | 12 | 13 | 8 | 12 | 15 | 10 | 13 | 9 | 8 | 15 | 8 | 15 | 11 |
| 4 weeks (mm) | 11 | 10 | 14 | 12 | 18 | 9 | 9 | 9 | 11 | 12 | 13 | 8 | 12 | 14 | 9 | 13 | 9 | 8 | 15 | 8 | 14 | 11 |
| 5 weeks (mm) | 11 | 10 | 14 | 12 | 18 | 9 | 9 | 9 | 11 | 12 | 13 | 8 | 12 | 14 | 9 | 13 | 9 | 8 | 15 | 8 | 14 | 11 |
| 6 weeks (mm) | 11 | 9 | 14 | 12 | 18 | 8 | 9 | 9 | 11 | 10 | 12 | 8 | 12 | 14 | 9 | 12 | 9 | 8 | 15 | 8 | 14 | 11 |
| 7 weeks (mm) | 10 | 9 | 14 | 12 | 18 | 8 | 9 | 9 | 10 | 10 | 12 | 8 | 12 | 14 | 9 | 12 | 9 | 8 | 14 | 8 | 14 | 11 |
| 8 weeks (mm) | 11 | 9 | 13 | 12 | 18 | 8 | 9 | 9 | 10 | 9 | 12 | 8 | 12 | 14 | 9 | 12 | 9 | 8 | 13 | 8 | 14 | 11 |

| | Example and Comparative Example | | | | | | | | | |
|---|---|---|---|---|---|---|---|---|---|---|
| | | | | | | | | | Comp. Ex. | |
| | 23 | 24 | 25 | 26 | 27 | 28 | 29 | 30 | 1 | 2 |
| After 1 week (mm) | 9 | 15 | 17 | 19 | 17 | 15 | 15 | 13 | 0 | 8 |
| 2 weeks (mm) | 9 | 13 | 15 | 16 | 15 | 13 | 13 | 10 | 0 | 0 |
| 3 weeks (mm) | 8 | 13 | 15 | 16 | 15 | 13 | 13 | 10 | 0 | 0 |
| 4 weeks (mm) | 8 | 13 | 14 | 16 | 15 | 12 | 13 | 10 | 0 | 0 |
| 5 weeks (mm) | 8 | 13 | 14 | 14 | 15 | 12 | 13 | 10 | 0 | 0 |
| 6 weeks (mm) | 8 | 13 | 14 | 14 | 15 | 10 | 13 | 10 | 0 | 0 |
| 7 weeks (mm) | 8 | 13 | 14 | 14 | 14 | 10 | 12 | 10 | 0 | 0 |
| 8 weeks (mm) | 8 | 13 | 14 | 14 | 14 | 10 | 10 | 8 | 0 | 0 |

What is claimed is:

1. A bioactive substance control-releasing resinous composition comprising an acrylic resin having both main chain and side chains, at least one side chain bearing at the end portion thereof, at least one group represented by the formula:

$$-X+O-M-(R_2)m]p$$

wherein:
X is

M is Al, Cu, Ti or Zn;
p is 1
m is an integer of 1 to 3
$R_2$ is a residue of organic acid having a biological activity which is connected through

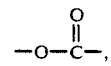

to the metal M and the metal content of the resin being 0.9 to 21.0% by weight of the total weight of the resin.

2. The bioactive substance according to claim 1 wherein M is Al.